(12) United States Patent
Li et al.

(10) Patent No.: US 8,536,523 B2
(45) Date of Patent: Sep. 17, 2013

(54) DESORPTION AND IONIZATION METHOD AND DEVICE

(75) Inventors: Ding Li, Manchester (GB); Wenjian Sun, Shanghai (CN)

(73) Assignee: Shimadzu Research Laboratory (Shanghai) Co. Ltd., Shanghai (CN)

( * ) Notice: Subject to any disclaimer, the term of this patent is extended or adjusted under 35 U.S.C. 154(b) by 221 days.

(21) Appl. No.: 13/265,638

(22) PCT Filed: Apr. 12, 2010

(86) PCT No.: PCT/CN2010/071690
§ 371 (c)(1),
(2), (4) Date: Oct. 21, 2011

(87) PCT Pub. No.: WO2010/121518
PCT Pub. Date: Oct. 28, 2010

(65) Prior Publication Data
US 2012/0037797 A1    Feb. 16, 2012

(30) Foreign Application Priority Data

Apr. 24, 2009   (CN) .......................... 2009 1 0301805

(51) Int. Cl.
*H01J 49/04*   (2006.01)
(52) U.S. Cl.
CPC ....................................... *H01J 49/04* (2013.01)
USPC ....................................................... 250/288
(58) Field of Classification Search
USPC ....................................................... 250/288
See application file for complete search history.

(56) References Cited

U.S. PATENT DOCUMENTS 6,140,639 A * 10/2000 Gusev et al. .................. 250/288
7,129,483 B2   10/2006 Youngquist et al.
(Continued)

FOREIGN PATENT DOCUMENTS

| CN | 101201335 A | 6/2008 |
| CN | 101520432 A | 9/2009 |
| EP | 1536452 A1 | 6/2005 |
| WO | 2008073146 A2 | 6/2008 |

OTHER PUBLICATIONS

Markus Haapala et al., Desorption Atmospheric Pressure Photoionization, Analytical Chemistry, Oct. 15, 2007, p. 7867-7872, vol. 9, No. 20.

(Continued)

*Primary Examiner* — Kiet T Nguyen
(74) *Attorney, Agent, or Firm* — Morris Manning & Martin LLP; Tim Tingkang Xia, ESq.

(57) ABSTRACT

The present invention involves a method and a device for sequentially desorbing and ionizing mixed analytes on a solid surface with a gradual temperature scan, and continuously collecting data for multiple times in the gradual desorption and ionization process. By gradually increase the temperature of at least one part of the sample, the analytes with different thermal desorption capabilities are sequentially desorbed from surfaces of the solid sample, thereby providing a sample pre-separation scheme, so as to reduce difficulties to subsequent mass spectrum detection. Meanwhile, since mass spectrum data of the analytes with different boiling points is collected for multiple times during a temperature scan, the analytes with a low boiling point can be detected first at lower temperature in order to avoid rapid exhaustion at higher temperature, thereby improving the detection efficiency of the analytes with low boiling points.

19 Claims, 3 Drawing Sheets

(56) References Cited

U.S. PATENT DOCUMENTS

| | | |
|---|---|---|
| 7,582,863 B2 * | 9/2009 | Picard et al. .............. 250/288 |
| 2007/0187589 A1 | 8/2007 | Cooks et al. |
| 2008/0142701 A1 | 6/2008 | Prest |
| 2009/0159790 A1 | 6/2009 | Kostiainen et al. |
| 2010/0044560 A1 * | 2/2010 | Basile et al. .............. 250/282 |

OTHER PUBLICATIONS

Robert B. Cody et al., Versatile New Ion Source for the Analysis of Materials in Open Air under Ambient Conditions, Analytical Chemistry, Apr. 15, 2005, p. 2297-2302. vol. 77, No. 8.

Zoltán Takáts et al., Mass Spectrometry Sampling Under Ambient Conditions with Desorption Electrospray Ionization, Science, Oct. 15, 2004, p. 471-473, vol. 306.

Jentaie Shiea et al., Electrospray-assisted laser desorption/ionization mass spectrometry for direct ambient analysis of solids, Rapid Communications in Mass Spectrometry, 2005, p. 3701-3704, vol. 19.

Joshua J. Coon et al., Atmospheric pressure laser desorption/chemical ionization mass spectrometry: a new ionization method based on existing themes, Rapid Communications in Mass Spectrometry, 2002, p. 681-685, vol. 16.

Charles N. McEwen et a., Analysis of Solids, Liquids, and Biological Tissues Using Solids Probe Introduction at Atmospheric Pressure on Commercial LC/MS Instruments, Analytical Chemistry, Dec. 1, 2005, p. 7826-7831, vol. 77, No. 23.

\* cited by examiner

DESORPTION AND IONIZATION METHOD AND DEVICE

FIELD OF THE INVENTION

The present invention relates to mass spectrum technologies, and more particularly to a desorption and ionization method and device used for ion analysis under atmospheric pressure.

BACKGROUND OF THE INVENTION

With the wide application of a liquid chromatography-mass spectrometry system analyzing complex mixture, ion sources operating in an atmospheric pressure, such as an electrospray ion source and an atmospheric pressure chemical ionization source, are critical to fields such as food safety, environmental protection and national security. However, in the analysis process, preprocessing before the samples are introduced into the analysis system costs a great deal of time, hindering real-time and fast operations of the analysis technologies in the industrial fields. This problem is partially solved with the appearance of some advanced direct analysis methods such as Desorption Electrospray Ionization (DESI, Science, vol. 306, P471 (2004)) and Direct Analysis in Real Time (DART, Analytical Chemistry, vol. 77, P2297 (2005)).

Afterwards, some other sample direct analysis technologies under the atmospheric pressure also achieved certain success, for example, ionization technology using heated gas for sample desorption includes an Atmospheric Solid Analysis Probe (ASAP), a Desorption Corona Beam Ionization and a Desorption Atmospheric Pressure Photoionization (DAPPI) technology introduced respectively in Analytical Chemistry, vol. 77, P7826-P7831 (2005), and Analytical Chemistry, vol. 79, P7867-P7872 (2007), in which, the former two uses corona discharge, while the latter one uses vacuum-ultraviolet light to assist ionization, and particularly analyzes non-polar and low-polar small molecule which is hard to be ionized through DESI successfully.

Meanwhile, in order to increase spatial resolution of a section where the sample is desorbed, an atmospheric pressure direct analysis method (Electrospray-assisted laser desorption ionization (ELDI)) using an ultraviolet laser as a desorption tool and using an electrospray plume as an ionization tool is introduced in Rapid Communication in Mass Spectrometry, vol. 19, P3701-P3704 (2005). In the method, since the laser is used as a desorption source, the desorption area of the surface of the sample can be well controlled, which enables imaging studies with mass spectrometry under atmospheric pressure. The similar technologies based on IR laser desorption technology such as laser desorption chemical ionization (LDCI) technology (using an atmospheric pressure chemical ionization source as the ion source) and laser desorption photoionization (LDPI) technology (using an atmospheric pressure photoionization source as the ion source) have been described in Rapid Communication in Mass Spectrometry, vol. 16, P681-P685 (2002) and in China patent (application No. 200810033974.4), respectively. And these sources are complementary to the above ELDI method due to their ionization capabilities on low-polar molecules.

However, since a separation step is removed before ionizing the complex mixture, the probability of mass spectrum peaks overlapping for different constituents is greatly increased, which produces difficulties in spectrum analysis. Taking the ionization method using heating gas for thermal desorption for example, when high heating temperature is used, each constituent of the mixture will be desorbed at the same time, causing congestion of mass spectrum peaks for different constituents. Meanwhile, as for the constituent capable of being desorbed in low temperature, the sample may be rapidly exhausted in high desorbing temperature, thereby affecting analysis efficiency of a mass spectrometer for the constituent. Therefore, how to separate a mixture during ionization to a certain extent or desorb the mixture with special focus on certain chemicals in order to improve the detection efficiency and accuracy of the mass spectrometer for a sample mixture is an issue in need of urgent solution.

SUMMARY OF THE INVENTION

An objective of the present invention is to provide a desorption and ionization method used in a mass analyzer or other ion analyzers. In this method, by controlling the desorption conditions, the desorption process of a mixture can be performed step by step, thereby improving analysis efficiency and sensitivity. Another objective of the present invention is to provide a desorption and ionization device used in a mass spectrometer or other ion analyzers.

In order to solve the above problems the current invention adopted a technical solution for providing an atmospheric desorption and ionization method and device used for a mass spectrometer or other ion analyzers. The feature of the current invention includes: enabling temperature of at least one part of sample to gradually rise through a certain method, so that multiple analyzed constituents in the part of sample are sequentially desorbed; ionizing the desorbed analyzed constituents near the sample; and introducing ions of the analyzed constituents into the ion analyzer and enabling the ion analyzer to continuously collect data for multiple times during the temperature scan.

As one solution of the present invention, the temperature scan method for desorption includes: blowing heated gas to the sample, and gradually increasing the temperature of the heated gas, so that the temperature of at least one part of the sample can be gradually raised.

As another technical solution of the present invention, the ions obtained through the desorption and ionization method using the heated gas for desorption may be detected through a mass spectrometer or an ion mobility spectrometer, and are particularly applicable to being detected through a differential mobility spectrometer for continuous analysis under atmospheric pressure, in order to obtain information such as the spatial confirmation of the sample ions.

As another embodiment of the present invention, the desorption method with temperature scan includes: irradiating an infrared laser beam onto the sample, and controlling intensity, pulse width or repetition rate of the laser, so that the temperature of the irradiated part of the sample can be gradually raised, and multiple analyzed constituents in the part of sample are further sequentially desorbed; ionizing the desorbed analyzed constituents near the sample; and introducing the ions of the analyzed constituents into the mass spectrometer, and enabling the mass spectrometer to continuously collect spectra for many times during the temperature rising process.

In the above desorption and ionization method, in the situation where the desorption process involves the samples with abundant quantity or multiple similar mixing samples, the temperature scan control manner may be determined according to actual conditions in order to increase the efficiency for sample analysis and utilization of the constituents of the mixture. For example, the temperature scan for the first sample is achieved in a linear fashion, and the temperature scan procedure of the subsequent samples is determined according to the temperature of the peaks during the first scan. The process may be described in detail in the embodiment.

The methods for ionizing the analyzed constituents include: interacting charged particles or excited-state particles formed during corona discharge at the tip of a metal gas flow tube with molecules of the analyzed constituents; interacting charged particles formed through electrospray with the molecules of the analyzed constituents; and irradiating ultraviolet light onto the desorbed analyzed constituents for photoionization.

In order to solve the above problems, the present invention further provides a desorption and ionization device for ion analysis, which includes: a gas source and a heating device in communication with the gas source; a gas outlet, for forming a heated gas flow beam; a sample holder, for enabling at least one part of the sample to face the heated gas flow beam and to be desorbed; an ionization device, placed near the sample, for producing charged drops, ions, excited-state atoms or ultraviolet light to interact with and ionize the molecules of the desorbed analyzed constituents; an ion introduction device, for introducing the ions of the analyzed constituents into an analyzer for analysis; and a set of temperature measuring and control device, for controlling temperature of the gas heating device, so that the temperature of the gas heating device can be gradually raised during multiple data acquisition processes of an ion analyzer. Meanwhile, in order to prepare the heating device for the next temperature scan in a short period of time, the device is further configured with a cooling mechanism for fast cooling the heating tube.

In order to solve the above technical problems, as another embodiment the present invention further provides another desorption and ionization device for ion analysis, which includes: a laser and a device for controlling the intensity, pulse width and repetition rate; a sample holder, for enabling a laser to irradiate onto at least one part of the sample to cause analyzed constituents in the sample being ionized; an ionization device, placed near the sample, for producing charged drops, ions, excited-state particles or ultraviolet light to interact with molecules of the desorbed analytes for ionization; and an ion introduction device, for introducing the ions of the analyzed constituents into a mass spectrometer for analysis, in which the laser intensity, pulse width or repetition rate can control temperature of the irradiated sample for gradual increase during multiple data collection processes of a mass spectrometer.

The present invention has the following distinguished advantages in comparison with the prior art due to the above technical solutions. 1. The desorption temperature of the ion source is changed with time, so that the detected objects with different thermal desorption capabilities can be sequentially desorbed from the surface of the sample, thereby providing a pre-separation method for sample mixture to reduce difficulties for the subsequent mass analysis.

2. In the mean time, the method of collecting multiple data acquisitions for each constituent of the sample mixture (with different boiling points) in the temperature scan process is used. In such case, the detected analyte with a low boiling point may not be rapidly exhausted due to high temperature, thereby improving its detection efficiency.

BRIEF DESCRIPTION OF THE DRAWINGS

In order to clearly demonstrate the objectives, features, and advantages of the present invention, the present invention is illustrated in further details below with reference to the accompanying drawings, wherein.

DETAILED DESCRIPTION OF THE INVENTION

Figure 1:
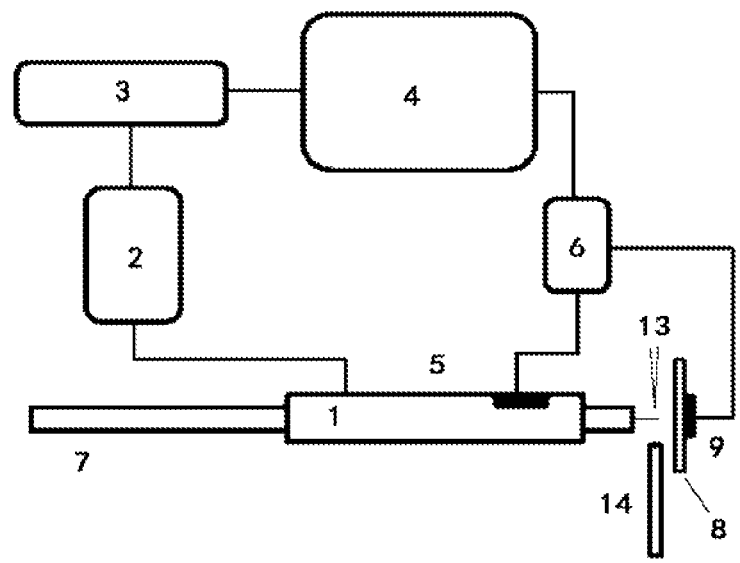
FIG. 1 is a schematic view of a desorption and ionization device according to a preferred embodiment of the present invention.
Figure 3:
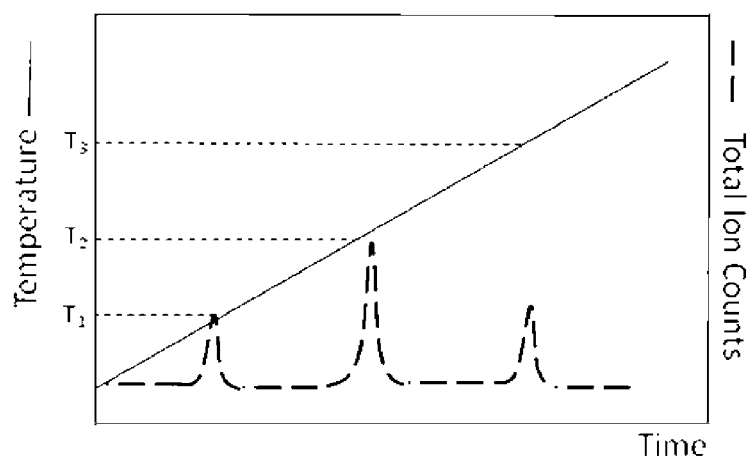
FIG. 3 is a schematic view of a preferred temperature scan process according to the present invention.

The present invention is applicable to desorbing and ionizing detected solid mixture samples attached to various solid surfaces. In a preferred embodiment of the present invention, a desorption process of the solid samples may be achieved through thermal desorption with a heated gas stream. FIG. 1 is a schematic view of controlling temperature of gas stream according to a preferred embodiment of the present invention, which includes a gas heating tube 1, a power source 2 for supplying power for the gas heating tube 1, a power source output power controller 3, a computer 4, a temperature sensor 5, and an analog-to-digital (A/D) converter 5 for receiving a signal of the temperature sensor. Gas supplied by a gas source enters the gas heating tube 1 through a gas pipe 7. The temperature of the gas heating tube 1 may be adjusted with time by controlling the output power of the power source 2 of a heater, so that the temperature of the desorption gas is adjusted. The temperature varying with the time is measured with the temperature sensor 5, and then is transmitted to the computer 4 through the A/D converter 6. The temperature of the gas heating tube 1 is further adjusted with the control of temperature control software which may linearly change the temperature of the gas flowing through the gas heating tube 1 as shown in FIG. 3. At this time, compounds with different boiling points in the mixture samples on a sample holder 8 can be sequentially desorbed along raising the gas temperature. For example, a boiling point of a compound A is the lowest, so the compound A can be desorbed at temperature $T_1$ and then is ionized. The compound B has a higher boiling point than that of the compound A, so higher desorption temperature is required, and the compound B is desorbed at temperature $T_2$ and then is ionized. Likewise, the desorption temperature $T_3$ for a compound C with the highest boiling point is the highest. With the rising of the temperature, different compounds are separated in time (or in the temperature axis), which provides more chemical information for the analysis of the compounds mixture and reduces the loads of downstream mass analyzer and complexity of data analysis. The loads and complexity include excessively dense mass peaks on a mass spectrum for difficult data interpretation, and influence of space charge effect caused by excessive ions in some mass spectrometers such as an ion trap mass spectrometer. A procedure for heating the sample by using the heated gas stream may be set through programming the duty cycle of a heater and the voltage of the heater in advance after measurement and calibrations. During the measurement and calibration processes, a temperature sensor 9 mounted on the sample holder 8 measures a signal indicating temperature rise, and compares the obtained scan with the required scan, and then further adjusts a temperature rising control procedure, so that the scan meets the actual requirements. Afterwards, a sample holder 8 with the same thermal conductivity and thermal capacity can be selected for sample analysis in order to achieve a similar temperature scan process compared to the calibration temperature scan process.

In this embodiment, the sample holder 8 may be a thin plate made of stainless steel. When the sample is desorbed by the hot gas, the temperature of the thin plate rises, so the temperature sensor 9 mounted at the back of the plate may feed back the temperature signal to the computer in real time, thereby further controlling the desorption temperature.

Figure 4:
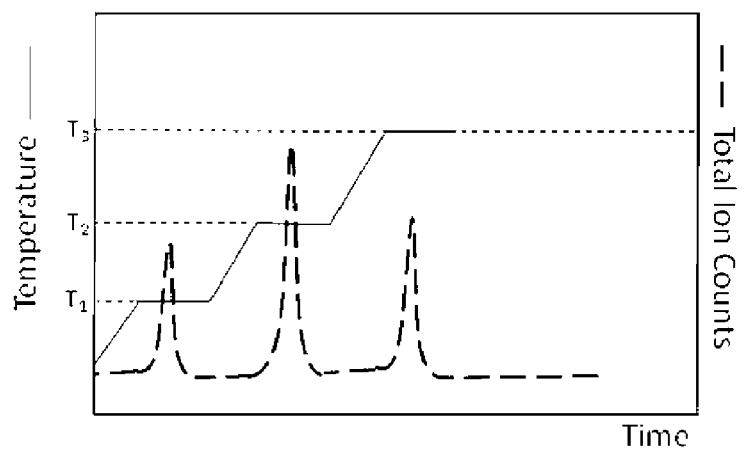
FIG. 4 is a schematic view of another preferred temperature scan process according to the present invention.

During the analysis of the samples with sufficient content or multiple samples of the same kind, in order to improve analysis speed and utilization of each constituent in the sample, the temperature rising control manner may be determined according to actual conditions. As shown in FIG. 3 and FIG. 4, the computer automatically captures the temperature of peaks of the mass spectra during temperature scanning for the first time (FIG. 3), and the speed of scanning a segment without a peak and non-target compounds (peaks from chemical noises) would be accelerated during the temperature scan in the next cycle, Meanwhile, the temperature of a segment containing targeted peaks during a scan would stay for a while, so that the compound corresponding to the temperature can be fully desorbed. Since in the subsequent scan the duration for which the desorption temperature stays at each segment containing targeted peaks can be longer than that for the first scan, an integrated area of the mass spectrum peaks can be correspondingly increased.

After temperature scan is ended, in order to enable the gas heating tube 1 to be rapidly cooled for the convenience of the next scan, a great deal of cooling gas may be introduced into the gas heating tube 1. For example, when the gas is helium, nitrogen with low cost may be used as the cooling gas, or a certain amount of water or organic solvent may be introduced into the gas heating tube 1 for assisting cooling.

In the above preferred embodiment, an ionization method of the present invention may be one of the electrospray ionization, ultraviolet light ionization and corona discharge ionization. Referred to FIG. 1, a pointed tip for causing corona discharge may be disposed at an outlet of the gas heating tube, which may be a sharp terminal of a metal heating tube or as the needle 13 orthogonally placed as shown in FIG. 1. Ions and excited-state particles produced at the point tip are carried by the heated gas stream to form a corona beam blowing to the sample. When the sample is desorbed by the heated gas stream, molecules of the detected object desorbed into a gas phase may interact with the ions or the excited-state particles in the airflow and then are ionized. The produced ions may be desorbed and introduced into an inlet of a mass spectrometer 14 or other types of ion detector afterwards. The analytes desorbed in different temperature/laser power have much different polarities, and different ionization methods have different efficiencies due to different polarities of the analytes. For example, macromolecules with high polarity are easily ionized through the electrospray ionization, micromolecules with low polarity are easily ionized through ultraviolet light ionization, and the polarity of molecules capable of being ionized through the corona discharge ionization is between the two. Therefore, in a process of sequentially desorbing the sample, the above three ionization methods may be used correspondingly, so that the analytes with different chemical and physical characteristics can be further identified; or several of the above three ionization methods may be combined for use, so that the analytes with different chemical and physical characteristics can be ionized through an ionization method appropriate for each, thereby further improving ionization efficiency of the ion sources.

In order to obtain more information of a chemical structure of the detected objects, the ions obtained through the above desorption and ionization method may also be detected with a device other than a mass spectrometer. For example, it may be detected with an ion mobility spectrometer, and are particularly applicable to being detected through a differential mobility spectrometer for continuous analysis under atmospheric pressure. The size of a collision cross-section of the ion in the gas phase can be obtained with the differential mobility spectrometer, thereby deducing a spatial conformation under such a condition. Meanwhile, the method can provide fast sample pre-separation for further ion detection (for example, using a mass spectrometer).

Figure 2:
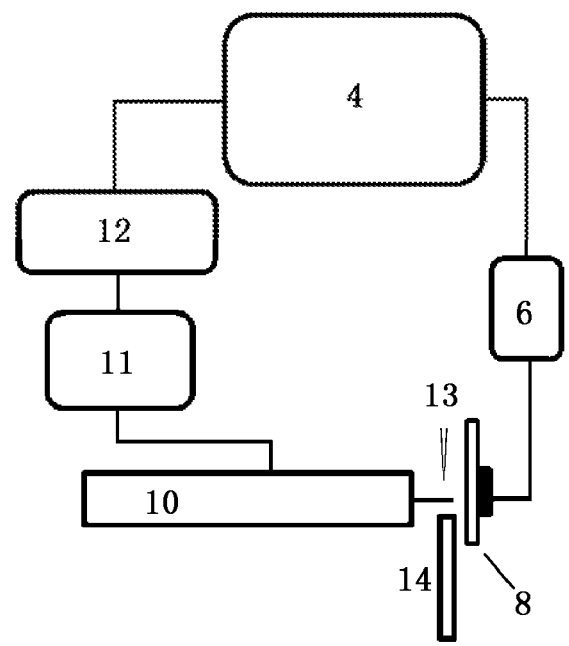
FIG. 2 is a schematic view of a desorption and ionization device according to another preferred embodiment of the present invention.

In another preferred embodiment of the present invention, a desorbing process of a solid sample analyte may also be completed through the thermal effect of an infrared laser. FIG. 2 is a schematic view of a device for performing desorption and ionization on a sample mixture by using the continuous infrared laser in this embodiment. The laser for desorbing the analyte may be a semi-conductor infrared laser 10 having a preferred wavelength range being 800 nanometers (nm)-1200 nm. The semi-conductor infrared laser 10 was generally operated in a continuous wave mode, but may also operate in a pulse mode by controlling switch-on or switch-off of a power source 11. Since the laser for sample desorption is the continuous infrared laser, a thermal effect produced after the continuous infrared laser irradiates onto a surface of a sample holder 8 may be controlled by modulating the output of the continuous laser. An output pulse width and a repetition rate of the laser may be controlled through a modulator 12 on the power source 11. When the pulse width or the-duty cycle is increased with analysis time, output power of the laser is also gradually increased, causing gradual temperature rising of the surface of the sample holder 8, which is similar to the sample heating method using the gas heating tube 1 in the previous embodiment. Of course, the thermal effect of the semi-conductor laser may be adjusted by directly controlling output current of the laser power source 11 and then changing laser intensity. The temperature rising procedure using the laser thermal effect may be set by programming the laser intensity, pulse width or repetition rate in advance and through actual measurement and calibration. During the calibration, a temperature sensor 9 mounted on the sample holder 8 measures the temperature rising, compares the obtained temperature-time relation with the required relation, and then further adjusts a laser control procedure, so that the temperature scan meets the actual requirements. Afterwards, the sample holder 8 with the same thermal conductivity and thermal capacity is selected for sample analysis, and then a scan being the same with a process during calibration can be achieved.

Similar to the above embodiment, the sample holder 8 may be a thin plate made of stainless steel. When the sample is desorbed by the laser, the temperature of the thin plate will increase and the temperature sensor 9 mounted at the back of the plate may feed back the temperature signal to the computer in real time, thereby further controlling the desorption temperature.

Meanwhile, when the laser is used as a desorption manner, similar to the above embodiment, the temperature rising control process may be determined according to actual conditions. The temperature in a time segment containing targeted peaks during a scan would stay for a while, while the speed of scanning a segment without a peak and non-target compounds (peaks from chemical noises) would be accelerated.

Similar to the first preferred embodiment, in this embodiment, an ionization method of the present invention may be one of the electrospray ionization, the ultraviolet light ionization and the corona discharge ionization. The ionization device in FIG. 2 uses the corona discharge ionization in the above ionization methods.

Figure 5:
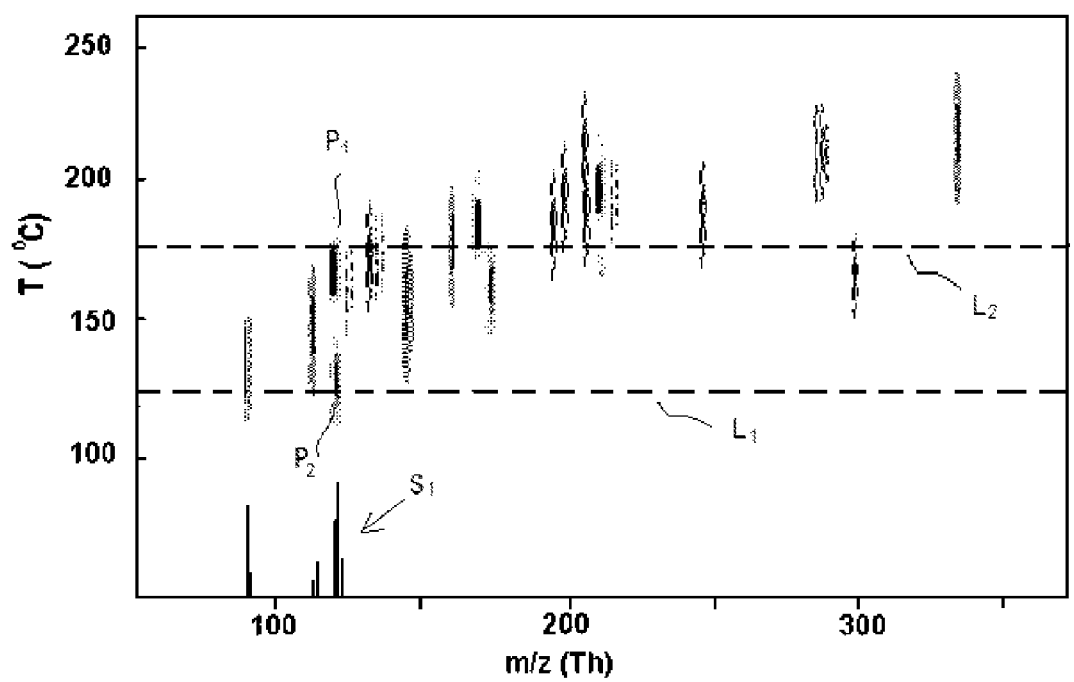
FIG. 5 is a plot of temperature vs. m/z indicated by the data according to the present invention.

A key step of the present invention is to use an ion detector such as a mass spectrometer to continuously perform spectrum collection, so as to obtain a two-dimensional distribution of desorption temperature and related spectra. FIG. 5 illustrates a schematic view indicating such a concept. As shown in FIG. 5, with the rise of the temperature, the mass distribution of the obtained spectrum peaks is changed, and the change indicates that different constituents of the compound need different desorption temperatures. The mass spectrum $S_1$ shown at the bottom of FIG. 5 is acquired at time when temperature reaches $T_1$. The dash lines indicates that the mass spectra are recorded on the 2D plot during the scan of temperature. The contents $P_1$ and $P_2$ have same mass to charge ratio, but they are desorbed at different temperature and therefore they can be distinguished by using the 2D plot.

The present invention is not limited to the above embodiment, persons with experience may conveniently design multiple implementation types according to the embodiment of the present invention. For example, the rising of temperature may be a non-linear process, so as to suit the mixed analytes of different kinds. The heating method may also not be limited to the methods of heating through a heater or a laser, and an ordinary infrared lamp or flame may be used for heating. The ionization on the sample may also not be limited to the ionization methods described in the above, and methods such as radiation induced ionization with radioactive materials or laser ionization may be used for the analytes with different characteristics. Any method or device for sequentially desorbing samples with a temperature scan, and subsequent post-ionization, ion introduction and data acquisition, regardless of the variation of the heating and ionization methods, shall all fall within the protection scope of the present invention.

What is claimed is:

1. An atmospheric pressure desorption and ionization method for mass spectrum analysis, comprising:
   enabling temperature of at least one part of a sample to gradually rise, so that multiple analyzed constituents in the part of the sample are sequentially desorbed;
   ionizing desorbed analyzed constituents near the sample; and
   introducing ions of the analyzed constituents into a mass spectrometer and enabling the mass spectrometer to continuously collect spectra for multiple times during the scan.

2. The desorption and ionization method according to claim 1, wherein the desorption method with temperature rising comprises: irradiating an infrared laser beam onto the sample, and controlling intensity, pulse width or repetition rate of the laser, so that the temperature of the irradiated part of the sample gradually rises.

3. The desorption and ionization method according to claim 1, wherein a temperature rising speed of at least one part of the sample is basically constant, a temperature upper limit can be preset, and the temperature upper limit is smaller than 500° C.

4. The desorption and ionization method according to claim 1, wherein a thermal desorption process comprises more than one temperature scans and sampling processes, and the subsequent temperature scan and sampling process comprises slowing down or pause at temperature at which a mass spectrum peak is obtained in the previous temperature scan.

5. The desorption and ionization method according to claim 1, wherein a method for ionizing the analyzed constituents comprises: interacting charged particles or excited-state particles formed from discharge with molecules of the analyzed constituents.

6. The desorption and ionization method according to claim 1, wherein a method for ionizing the analyzed constituents comprises: interacting charged particles formed from electronspray with molecules of the analyzed constituents.

7. The desorption and ionization method according to claim 1, wherein a method for ionizing the analyzed constituents comprises: irradiating an ultraviolet light source onto the desorbed analyzed constituents, so that photoionization occurs.

8. An atmospheric pressure desorption and ionization method used for ion analysis, comprising:
   blowing heated gas stream onto a sample, and enabling temperature of the heated gas to gradually rise, so that temperature of at least one part of the sample gradually rises, and multiple analyzed constituents in the part of the sample are further sequentially desorbed;
   ionizing desorbed constituents near the sample; and
   introducing ions of said constituents into an ion analyzer, and enabling the analyzer to continuously collect data for multiple times during the scan.

9. The desorption and ionization method according to claim 8, wherein the ion analyzer comprises a mass spectrometer, for performing mass spectrum analysis on the ions of the analyzed constituents.

10. The desorption and ionization method according to claim 8, wherein the ion analyzer comprises an ion mobility spectrometer, for performing mobility analysis on the ions of the analyzed constituents.

11. The desorption and ionization method according to claim 8, wherein the ion analyzer comprises a differential ion mobility spectrometer, for performing differential mobility analysis on the ions of the analyzed constituents.

12. The desorption and ionization method according to claim 8, wherein a temperature rising speed of at least one part of the sample is basically constant, a temperature upper limit can be preset, and the temperature upper limit is smaller than 500° C.

13. The desorption and ionization method according to claim 8, wherein a thermal desorption process comprises more than one temperature scans and sampling processes, and the subsequent temperature scan and sampling process comprises slowing down or pause at temperature at which a mass spectrum peak is obtained in the previous temperature scan.

14. The desorption and ionization method according to claim 8, wherein a method for ionizing the analyzed constituents comprises: interacting charged particles or excited-state particles formed from discharge with molecules of the analyzed constituents.

15. The desorption and ionization method according to claim 8, wherein a method for ionizing the analyzed constituents comprises: interacting charged particles formed from electronspray with molecules of the analyzed constituents.

16. The desorption and ionization method according to claim 8, wherein a method for ionizing the analyzed constituents comprises: irradiating an ultraviolet light source onto the desorbed analyzed constituents, so that photoionization Occurs.

17. An atmospheric pressure desorption and ionization ion source for ion analysis, comprising: a gas source, an electrical gas heating device, a gas flow tube outlet, a sample holding device, an ionization device, and an ion introduction device in communication with an ion analyzer, wherein a set of temperature measuring and controlling device controls temperature of the electrical gas heating device so that the temperature of the electrical gas heating device gradually rises during a data collecting process of the ion analyzer for multiple times; and the electrical gas heating device comprises a cooling mechanism, for fast cooling the electrical gas heating device after analysis.

18. The desorption and ionization ion source according to claim 17, wherein the gas flow tube outlet comprises a metal tube with a point-tip, a high voltage is applied on the metal tube, so that a great number of ions and excited-state atoms of the gas flow can be produced during discharge and can interact with desorbed analytes for ionization.

19. An atmospheric pressure desorption and ionization source for mass spectrum analysis, comprising: a laser, a laser focus lens, an ionization device, a sample holding device, an ionization device and an ion introduction device in communication with a mass spectrometer, wherein a set of laser intensity, pulse width and repetition rate control device controls laser intensity, pulse width and repetition rate, so that temperature of an irradiated sample gradually rises during a data collection process of the mass spectrometer for multiple times.

* * * * *